United States Patent [19]

Bockman

[11] Patent Number: 5,310,759
[45] Date of Patent: May 10, 1994

[54] METHODS OF PROTECTING AND PRESERVING CONNECTIVE AND SUPPORT TISSUES

[76] Inventor: Richard S. Bockman, 22 Spring St., Sag Harbor, N.Y. 11963

[21] Appl. No.: 929,197

[22] Filed: Aug. 12, 1992

[51] Int. Cl.$^5$ ............................................. A61K 31/557
[52] U.S. Cl. ..................................... 514/573; 514/549
[58] Field of Search ................. 424/422, 449; 514/573, 514/549

[56] References Cited

U.S. PATENT DOCUMENTS 4,066,787  1/1978  Okazaki et al. ........................ 424/317
4,621,100  11/1986  Lund et al. ............................ 514/573

OTHER PUBLICATIONS

R. Salvatori et al, "Prostaglandin El Inhibits Collagenase Gene Expression in Rabbit Synoviocytes and Human Fibroblasts", Endocrinology, vol. 131, No. 1, pp. 21-28.

R. Salvatori et al, "PG1 and its Stable Analog Misoprostol Inhibit Collagenase Expression in Fibroblasts and Synoviocytes," Journal Bone & Min. Res 6 (Suppl 1) S270, Aug. 1991, Abstract.

J. Kurland et al., "Limitation of Excessive Myelopoiesis by the Intrinsic Modulation of Macrophage-Derived Prostaglandin E," Science, vol. 199, Feb. 1978, pp. 552-555.

Y. Hakeda et al, "Prostaglandin El and F2a Stimulate Differentiation and Proliferation, Respectively, of Clonal Osteoblasic . . . Messengers in Vitro", Endocrinology, vol. 121, 1987, pp. 1966-1974.

M. Ernst et al, "Estradiol Effects on Proliferation, Messenger Ribonucleic Acid for Collagen and Insulin-like Growth . . . Calvariae and Long Bones," Endocrinology, vol. 125, No. 2, 1989, pp. 825-833.

L. Bergkvist et al, "The Risk of Breast Cancer After Estrogen and Estrogen-Progestin Replacement," New England Journal of Medicine, vol. 321, No. 5, pp. 293-297.

G. Goldberg et al, "Human Fibroblast Collagenase", Journal of Biological Chemistry, vol. 261, No. 14, May 1986, pp. 6600-6605.

E. Campbell et al, "Monocyte Procollagenase and Tissue Inhibitor of Metalloproteinases," Journal of Biological Chemistry, vol. 262, No. 33, Nov. 1987, pp. 15862-15868.

G. Herron et al, "Secretion of Metalloproteinases by Stimulated Capillary Endothelial", Journal of Biological Chemistry, vol. 261, No. 6, Feb. 1986, pp. 2810-2813.

Edward Harris, Jr., "Pathogenesis of Rheumatoid Arthritis", Rheumatoid Arthritis 54, pp. 905-942.

H. Georgescu et al, "HIG-82: An Established Cell Line from Rabbit Periarticular Soft Tissue, Which Retains the 'Activatable' Phenotype", In Vitro Cellular & Develop, Biology, vol. 24, No. 10, Oct. 1988, pp. 1015-1022.

B. Kirkham "Interleukin-1, immune activation pathways, and different mechanisms in osteoarthritis and rheumatoid arthritis", Annals of the Rheumatic Diseases, vol. 50, pp. 395-400.

(List continued on next page.)

*Primary Examiner*—Thurman K. Page
*Assistant Examiner*—Peter F. Kulkosky
*Attorney, Agent, or Firm*—Meltzer, Lippe, Goldstein, Wolf, Schlissel & Sazer

[57] ABSTRACT

In this invention methods are described by which prostaglandins of the $E_1$ class and compounds that mimic or induce cyclic adenosine monophosphate are used to block collagenase gene expression by cells responsible for connective and support tissue breakdown. The consequence of using pharmaceutically acceptable preparations of prostaglandin $E_1$, analogs of prostaglandin $E_1$ or cyclic adenosine monophosphate agonists or inducers of cyclic adenosine monophosphate is to preserve and protect connective and support tissues. These methods provide new treatment modalities useful in protecting humans and animals against connective and support tissue degradation that occurs in aging, osteoporosis and osteoarthritis.

9 Claims, 4 Drawing Sheets

OTHER PUBLICATIONS

R. Bucala et al, "Constitutive Production of Inflammatory and Mitogenic Cytokines by Rheumatoid Synovial Fibroblasts," J. Exp. Med., Rockefeller University Press, Mar. 1991, vol. 173, pp. 569–574.

K. Arai et al, "Cytokines: Coordinators of Immune and Inflammatory Responses", Annu. Rev. Biochem. 1990, vol. 59, pp. 783–836.

M. Goldring et al, "Interleukin 1 Suppresses Expression of Cartilage-specific Types II and IX Collagens and Increases Types I and III . . . Chondrocytes", J. Clinical Invest, vol. 82, Dec. 1988, pp. 2026–2037.

G. Tate et al, "Suppression of Acute Inflammation by 15 Methyl Prostaglandin E1," Laboratory Investigation, vol. 59, No. 2, pp. 192, 193, U.S. and Canadian Academy of Pathology, Inc., pp. 192–199.

I. Kobayashi et al, "Electron Microscopic Studies of the Cartilage-Pannus Junction in Rheumatoid Arthritis," Arthritis and Rheumatism, vol. 18, No. 5, 1975, pp. 475–483.

M. J. Pond et al, "Experimentally-induced Osteoarthritis in the Dog," Annals of the Rheumatic Diseases, Heberden Society, pp. 387–388.

J. P. Pelletier et al, "Collagenolytic Activity and Collagen Matrix Breakdown of the Articular Cartilage in the Pond-Nuki Dog Model of Osteoarthritis," Arthritis and Rheumatism, vol. 26, No. 7, Jul. 1983, pp. 866–874.

E. Harris et al, "Collagenases" (first of three parts), New England Journal of Medicine, vol. 291, No. 11, pp. 557–563.

M. L. Stephenson et al, "Stimulation of Procollagenase Synthesis Parallels Increases in Cellular . . . Recombinant Interleukin 1B or Phorbol Ester," Biochem & Biophysical Res. Comm., vol. 144, No. 2, 1987, pp. 583–590.

F. J. Rauscher III, et al "Fos-Associated Protein p39 Is the Product of the jun Proto-oncogene", Science, vol. 240, pp. 1010–1016.

A. Postlethwaite et al, "Modulation of Fibroblast Functions by Interleukin 1: Increased Steady-State Accumulation of Type I . . . Recombinant Interleukin 1a and B", J. of Cell Biology, vol. 106, 1988, pp. 311–318.

M. Shinmei et al, "The Role of Cytokines in Chondrocyte Mediated Cartilage Degradation," Journal of Rheumatology 1989 (Supp 18), pp. 32–34.

M. Goldring et al, "Modulation by Recombinant Interleukin 1 of Synthesis of Types I and III Collagens and Associated Procollagen . . . Human Cells," J. of Biological Chemistry, vol. 262, No. 34, Dec. 1987, pp. 16724–16729.

R. Lafyatis et al, "Interleukin-1 Stimulates and All-Trans-Retinoic Acid Inhibits Collagenase Gene Expression through . . . Binding Site." Molecular Endocrinology vol. 4, No. 7, pp. 973–980.

D. Brenner et al, "Prolonged activation of jun and collagenase genes by tumor ncrosis factor-a", Nature, vol. 337, Feb. 1989, pp. 661–663.

M. Imagawa et al, "Transcription Factor AP-2 Mediates Induction by Two Different Signal-Transduction Pathways: Protein . . . and cAMP". Cell, vol. 51, Oct. 1987, pp. 251–260.

M. Rednar et al, "Cyclic AMP-regulating agents inhibit endotoxin-mediated cartilage degradation", J. Biochem. vol. 244, pp. 63–68.

M. Madden et al. "Grafting of Cultured Allogeneic Epidermis on Second- and Third-degree Burn Wounds on 26 patients," Journal of Trauma, 1986, vol. 26, No. 11, pp. 955–962.

D. S. Newcombe et al, "Human synoviocytes: Activation and desensitization by prostaglandins and 1-epinephrine", Cell Biology, Aug. 1975, vol. 72, No. 8, pp. 3124–3128.

P. Angel et al, "12-o Tetradecanoyl-Phorbol-13-Acetate Induction of the Human Collagenase Gene Is Mediated by . . . 5'-Flanking Region", Mollecular & Cellular Biology, Jun. 1987, vol. 7, No. 6, pp. 2256–2266.

J. Case et al, "IL-1 Regulation of Transin/Stromelysin . . . C-Dependent Pathway" J. of Immunology, vol. 145, No. 11, Dec. 1990, pp. 3755–3761.

METHODS OF PROTECTING AND PRESERVING CONNECTIVE AND SUPPORT TISSUES

BACKGROUND OF THE INVENTION

A. Field of the Invention.

The present invention relates to methods of protecting and preserving connective and support tissues by utilizing prostaglandin $E_1$ ($PGE_1$) compounds or cyclic adenosine monophosphate (cAMP) agonists or inducers of endogenous cAMP to block collagenase gene expression. Since connective and support tissues, which comprise skin, bone, cartilage, fascia, tendons, ligaments and collagen containing elements that encapsulate organs, have as their major organic constituent the protein collagen, these methods provide new treatment modalities useful in protecting humans and animals against connective and support tissue degradation that occurs in aging, osteoporosis and osteoarthritis.

Several types of collagen exist: skin, bone, fascia, tendons and ligaments are comprised primarily of type I collagen; cartilage is largely comprised of type II collagen. Breakdown or degradation of these tissues requires the enzyme collagenase (EC 3,424.7), this unique neutral metalloproteinase is produced by cells normally present in connective and support tissues. In certain metabolic disorders or inflammatory diseases, increased levels of this enzyme is produced leading to the accelerated destruction or breakdown of connective and support tissues.

Only collagenase is currently known to be capable of the initial cleavage necessary to degrade type I, II and III collagens. Therefore, regulation of collagenase production can be a critical point at which to control connective and support tissue breakdown and thereby prevent the disorders that this breakdown causes. Examples of conditions or diseases caused by accelerated connective and support tissue breakdown include but are not limited to aging, osteoporosis and arthritis. Prior art approaches to preventing accelerated connective and support tissue breakdown have focused on regulating the effect of collagenase or providing replacement tissue. However, none of the prior art methods have been fully effective, universally applicable and risk free.

B. Description of the Prior Art.

In contrast to the methods of the present invention, prior art methods for protecting or preserving connective and support tissue focussed almost exclusively on preventing tissue inflammation. Previously described methods for blocking collagenase have utilized peptide inhibitors of the formed (previously synthesized) collagenase enzyme or agents that generally suppress immune or connective tissue metabolic function or are toxic for the tissues.

At the present time no specific therapies exist to prevent collagen breakdown associated with aging. In the skin the attritional loss of collagen from breakdown and decreased synthesis of new collagen results in a thinning and the loss of structural integrity. The consequence of these changes is a looseness and wrinkling of skin. Physicians have used injections of bovine collagen to temporarily restore skin fullness but this xenograft material is soon resorbed, that is, removed by immune cells. The injection of foreign collagen does not restore tissue strength as it is not incorporated into the normal architecture of the extracellular matrix. The injection of this foreign protein into the skin has been associated with severe immune reactions and has been reported to cause severe autoimmune responses clinically producing collagen vascular diseases that actually accelerate connective and support tissue breakdown. No proven therapies for preserving skin integrity by protecting skin collagen from collagenase-action have been reported.

The loss of the organic (collagen) and inorganic (mineral) matrices of bone characterizes the pathologic process that leads to osteoporosis. Several agents and drugs have been used to prevent the excessive breakdown of bone in order to treat osteoporosis. The efficacy of these treatment modalities has usually been assessed by following the mineral (calcium) content of bone or its loss from the body. Therapies have not been directed at preventing collagen breakdown as the means of protecting and preserving bone.

Calcitonin is a U.S. Food and Drug Administration approved medication for the treatment of low bone (mineral) mass. Calcitonin is a naturally produced hormone which in pharmacologic amounts can transiently inhibit bone resorbing cells (osteoclasts) and thereby block bone breakdown. This hormone acts via cell surface receptors to activate biochemical signals within the osteoclast leading to a decrease in metabolic activity.

Estrogen, the female sex steroid, is an approved medication for the treatment of postmenopausal osteoporosis. While its mechanism of action is not fully understood, it can induce bone cells to synthesize new collagen as well as endogenous growth factors such as insulin-like growth factor-1 (IGF-1) (Ernst, et. al, "Estradiol Effects on proliferation, messenger RNA for collagen and insulin like growth factor-1 and parathyroid hormone stimulated adenylate activity on osteoblastic cells from calvariae and long bone." *Endocrinology* 125:825–833 (1989)). However, the benefits of estrogen are limited to perimenopausal women and estrogen treatment is associated with increased risks of uterine and breast cancer (Bergkvist, et. al, "The risk of breast cancer after estrogen and estrogen-progestin replacement." *New Engl J Med.* 321:293–297 (1989)).

Recently, naturally produced substances have been discovered which promote growth and healing of connective and support tissues. Such substances have been termed growth factors. Growth factors, usually proteins, initiate programs of differentiation and/or development within an organism. Although growth factors would appear to be ideal for inducing support and connective tissue repair, such factors are not practically useful as pharmaceutical agents. Growth factors are proteins and like most proteins are not stable and tend to break down upon storage. As proteins, growth factors are not suitable for oral administration since they are digested and destroyed before entering the blood stream. Growth factors cannot be satisfactorily administered as topical ointments. As a result of the lability of growth factors the preferred route of administration is parenteral, that is, injected into the body or blood under medical supervision. Unfortunately, many of the growth factors are species specific and are recognized as foreign by other species. Thus, there is the constant danger of eliciting an immune response. Lastly, growth factors when administered parenterally, do not necessarily target to skin, connective and support tissues and are more likely to affect many different cells throughout the body. With the exception of certain recently described naturally occurring growth factors, there is no disclosure or suggestion in the prior art of pharmaceutically acceptable compounds that can protect and preserve connective and support tissues by preventing collagenase gene expression, the critical enzyme needed for collagen breakdown.

Osteoarthritis is a disease characterized by inflammation and degradation of the cartilage and subchondral (adjacent) bone in joints. The erosion of connective and support tissues is mediated in large part by proteolytic enzymes (including collagenase) released by cells involved in the inflammatory process within the joint. Collagenase is produced by most of the cell types found in inflamed joints including fibroblasts (Goldberg, G. L.; et. al, "Human fibroblast collagenase." *J. Biol Chem* 261:6600–6605 (1986)), monocytes and macrophages (Campbell, E. J.; et, al, "Monocyte procollagenase and tissue inhibitor metalloproteinases" *J. Biol Chem* 262 15862–15868 (1987)), endothelial cells (Herron, G. S.; et. al, "Secretion of metalloproteinases by stimulated capillary endothelial cells." *J. Biol Chem* 261:2810–2813 (1986)), and synoviocytes (Harris, Jr., E. D. "Pathogenesis of rheumatoid arthritis." In *Textbook of Rheumatology*, pp. 886–914, Kelly, W. N.; et. al, (eds.) (W. B. Saunders, Phil Pa. (1984); and Georgescu, H. I. "HIG-82 an established cell line from rat periarticular soft tissue which retains the 'activable' phenotype." *In Vitro Cell and Dev. Biol* 24:1015–1022 (1988)). Collagenase derived from the synoviocyte is thought to play a central role in mediating collagen and thus the cartilage destruction associated with osteoarthritic disorders (Krane, S. M.; et. al, "Mechanisms of matrix degradation in rheumatoid arthritis." *Ann NY Acad Sci* 580:340–354 (1990)).

A number of agents and drugs have been employed to prevent and treat the cartilage and bone destruction occurring in joints affected by osteoarthritis. Principle amongst these agents and drugs are steroidal and non-steroidal anti-inflammatory agents and drugs. Steroids include glucocorticoids, hormones produced by the adrenal cortex and the more potent synthetic analogs of these hormones. These agents have many anti-inflammatory activities including the ability to inhibit the proliferation or activity of the immune cells that produce cytokines capable of stimulating collagenase synthesis, release and activation. Unfortunately, anti-inflammatory steroids have a potent catabolic effect on matrix producing cells, therefore they block the synthesis of new matrix components. The consequence of such treatment is the thinning and weakening of connective and support tissues as well as a decreased ability of these tissues to repair themselves.

Non-steroidal anti-inflammatory agents (NSAIDS) such as aspirin, acetaminophen, ibuprofen, flurbiprofen, etc. act by inhibiting the synthesis or action of key "second messengers" such as prostaglandins. These second messengers carry the "inflammatory signal" to effector cells capable of breaking down connective and support tissues (Vane, J. R. "Prostaglandins as mediators of inflammation." In *Advances in Prostaglandin and Thromboxane Research*, pp. 791–801, B. Samuelsson and R. Paoletti (eds.), Raven Press NY (1976)). In principle, blocking the signal-chain should prevent the synthesis and activation of the effector molecules that are directly responsible for connective and support tissue destruction. Unfortunately, many signal pathways exist and agents such as the NSAIDS are not effective in fully blocking the inflammatory response seen in osteoarthritic joints nor have they been proven to prevent the connective and support tissue destruction that characterized degenerative joint disease such as osteoarthritis. NSAIDS do not act by inhibiting collagenase gene expression, indeed to one skilled in the art, it is evident based on the data presented in this disclosure that blocking $PGE_1$ with NSAIDS would block the beneficial effects of $PGE_1$ which is to suppress collagenase gene expression.

Considerable scientific interest has focused on naturally occurring and synthetic molecules which inhibit neutral metalloproteinases. This class of neutral enzymes, of which collagenase is the prime example are thought to be critical for connective and support tissue breakdown. Natural and synthetic inhibitors have been found capable of blocking the activity of endogenously synthesized, active enzyme collagenase. These inhibitors act directly on the formed enzyme to chemically block its activity, these inhibitors do not act at the level of gene expression. Unfortunately, at the present time, no pharmaceutically acceptable or therapeutically effective collagenase inhibitor is available. Furthermore, should such a compound be produced, there is no indication that it could be properly targeted to connective and support tissues. Cartilage for example is essentially devoid of a vascular supply making drug delivery difficult. Many of the potent, naturally occurring metalloproteinase inhibitors are small peptides. As mentioned earlier with regard to "growth factors" such inhibitor peptides would require parenteral administration and are potentially immunogenic which makes the likelihood that they would be acceptable therapeutic agents remote. Up until the present invention there has been no fully acceptable method for inhibiting the expression of collagenase, the critical enzyme that causes connective and support tissue breakdown. With the exception of certain recently described naturally occurring growth factors, there is no disclosure or suggestion in the prior art of a pharmaceutically acceptable compound that can block collagenase gene expression in connective and support tissues and thereby reduce collagenase activity.

Moreover, the prior art appears to teach away from the findings of the present invention. Prostaglandins are hydroxylated fatty acids which can be produced by many tissues in the body usually in response to inflammatory stimuli. Prostaglandins have been characterized as mediators of inflammation and are thought to be involved in the accelerated connective and support tissue breakdown associated with rheumatic disorders. Prostaglandins of the $E_2$ class, the class most commonly produced by mammalian cells and the class most commonly studied, stimulate collagenase activity in cells derived from connective and support tissues. Thus, in contrast to prior disclosures that prostaglandins of the $E_2$ class stimulate collagenase activity, one novel aspect of the present invention is that prostaglandins of the $E_1$ series can actually block collagenase activity and that prostaglandin $E_1$ and cyclic adenosine monophosphate block collagenase activity by inhibiting collagenase gene expression.

SUMMARY OF THE INVENTION

The present invention involves methods of protecting and preserving connective and support tissues by administering to a human or animal subject experiencing the breakdown of skin, bone, cartilage, fascia, tendons and ligaments as a result of aging, metabolic disorders such as osteoporosis or an inflammatory disorder or degenerative joint disease such as osteoarthritis a pharmaceutically acceptable prostaglandin $E_1$ (or prostaglandin $E_1$ analog) or a cyclic adenosine monophosphate agonist or inducer-compound in an amount sufficient to selectively block metalloproteinase (such as, collagenase or stromelysin) gene expression so as to reduce the activity of neutral metalloproteinase responsible for connective and support tissue breakdown.

By blocking connective and support tissue, the methods of the present invention are also useful with respect to both humans and animals: in improving the cosmetic appearance of skin in humans and animals by improving wound healing and repairing skin damage comprising injuries, acne, aging, ultraviolet damage, burns, acquired disorders and removing wrinkles, folds redundancies; and in enhancing attachment, fixation and stabilization of implants and prosthetic devices, for example, skin grafts, bone grafts, prostheses, cartilage grafts, tendon grafts and fascia grafts, which are placed in the body to strengthen or repair damaged tissues; skin grafts, bone grafts, prostheses, cartilage grafts, tendon grafts and fascia grafts.

A recently published article by Salvatori, R.; Guidon, Jr., P. T.; Rapuano, B. E. and Bockman, R. S., entitled "Prostaglandin $E_1$ Inhibits Collagenase Gene Expression in Rabbit Synoviocytes and Human Fibroblasts" and published in *Endocrinology* 131:001–008 (1992), describes some of the early research disclosed herein and is hereby incorporated herein.

In accordance with the present invention, the inhibitory actions of prostaglandin $E_1$ and its analogs (for example, 15 methyl and 16 dimethyl prostaglandin $E_1$ compounds) are used to protect and preserve connective and support tissues by preventing the formation of the enzyme (collagenase) which is necessary for collagen breakdown.

Also in accordance with the present invention, is the method of treating connective and support tissues with cyclic adenosine monophosphate (cAMP), its analoqs (for example, 8-Bromocyclic adenosine monophosphate) and its inducers or compounds able to raise endogenous cellular cAMP levels (for example, phosphodiesterase inhibitor - 3 isobutyl 1-methylxanthine (IBMX)) or activators of endogenous adenyl cyclase (for example, forskolin (FORS)) in order to prevent tissue breakdown leading to aging, osteoporosis and arthritis.

DESCRIPTION OF THE PREFERRED EMBODIMENTS

Applicant has found that pharmaceutically acceptable prostaglandin $E_1$ (or prostaglandin $E_1$ analogs) and cyclic adenosine monophosphate agonists and inducers can selectively inhibit metalloproteinase (collagenase) gene expression in human and animal cells. Applicant believes that the use of these agents can also be effective in inhibiting stromelysin gene expression in human and animal cells. These novel findings provide the basis for the new methods of the present invention which are used for protecting and preserving connective and support tissues from breakdown as seen in aging, osteoporosis and arthritis.

The mechanism by which prostaglandin $E_1$ and its analogs or cyclic adenosine monophosphate inducers block collagenase gene expression is believed to be the same in all connective and support tissues. For the purpose of illustration, this new method of preserving and protecting connective and support will be described by discussing osteoarthritis, its pathogenesis and its treatment. The following disclosure is meant to describe the underlying mechanisms of connective and support tissue destruction and how applicant believes the methods of the present invention prevent and protect against such destruction. Using osteoarthritis as the model disorder is not meant to imply that the use of the current invention is restricted to this application alone. Rather, it should be evident to one skilled in the field that the present invention is applicable but not limited to disorders associated with aging and metabolic disorders of connective and support tissues.

A. Connective and Support Tissue Destruction in Osteoarthritis

Chronic inflammatory disorders of joints such as in rheumatoid or osteoarthritis inevitably results in localized destruction of cartilage and bone, two examples of connective and support tissues. Inflammation with activated immune cells in the synovium often characterizes active joint disease and is associated with increased production and release of potent cytokines that initiate and amplify connective tissue destruction (Kirkham, B. "Interleukin-1. Immune Activation Pathways and Different Mechanisms In Osteoarthritis and Rheumatoid Arthritis." *Ann Rheum Dis* 50(6):395–400 (1991) and Bucala, R.; Ritchlin, C.; Winchester, R. and Cerami, A. "Constitutive Production of Inflammatory and Mitogenic Cytokines By Rheumatoid Synovial Fibro blasts." *J. Exp Med* 173(3):569–74 (1991)). Principle cytokines thought to be important in mediating the connective tissue destruction include Interleukin-1 (IL-1) and tumor necrosis factor (TNF), both of which increase the synthesis of matrix metalloproteinases (MMP) such as collagenase (EC 3.4.24.7, (MMP-1)) and stromelysin (EC3.4.24.17, (MMP-3)). These enzymes are thought to be directly responsible for bone and cartilage degradation (Lipsky, P. E.; Davis, L. S.; Cush, J. J. and Oppenheimer-Marks, N. "The Role of Cytokines in The Pathogenesis of Rheumatoid Arthritis." *Springer Semin Immunopathol.* 11:123–836 (1989) and Arai, K.; Lee, F.; Miyajima, A.; Miyatake, S.; Arai, N. and Yokota, T. "Cytokines: Coordinators of Immune and Inflammatory Responses." *Ann Rev Biochem* 59:783–836 (1990)). The cytokines IL-1 and TNF can also decrease chondrocyte and osteoblast synthesis of key matrix proteins such as Types I, II and IX collagen and proteoglycans (Saklatvala, J. and Bird, T. A. "Effects of tumor necrosis factor-alpha and Interleukin-1 on the proteoglycan matrix of cartilage." In *Development and Diseases of Cartilage and Bone Matrix*, pp. 291–298, Alan R. Liss, Inc. pub. (1987) and Goldring, M. B.; Birkhead, J.; Sandell, L. J.; Kimura, T.; Krane, S. M.; "Interleukin-1 suppresses expression of cartilage-specific types II and IX collagens and increases types I and III collagens in human chondrocytes." *J Clin Invest* 82:2026–2037 (1988)). Lastly, these cytokines can induce other cells within the joint space to produce factors that lead to abnormal cell differentiation and proliferation aggravating the pathologic changes that are occurring within the joint. The consequences of acute and or chronic inflammation in the arthritic joint are three fold: (1) accelerated matrix destruction, (2) inhibition of matrix repair, and (3) dysplastic tissue responses. Clinically, the problem presents itself as progressive joint destruction that is associated with chronic pain and disability.

Recent studies of synovial cells, fibroblasts and bone explants have examined the effects of E class prostaglandins, hydroxylated fatty acids derived from the metabolism of membrane phospholipids. Specific prostaglandins such as prostaglandin $E_2$ ($PGE_2$) are endogenously synthesized by many of the joint tissues and can have multiple effects on cartilage and bone metabolism. Other members of the PGE family, notably prostaglandin $E_1$ ($PGE_1$) have not been reported to be produced by these tissues, and the exogenous application of $PGE_1$ has produced an anti-inflammatory effect (Tate, G.; Mandell, B. F.; Schumacher, Jr., H. R. and Zurier, R. B. "Suppression of acute inflammation by 15 methyl Prostaglandin $E_1$." *Lab Invest* 59: 192–196 (1988)). Studies described in this application and in Salvatori, R.; Guidon, Jr., P. T.; Rapuano, B. E. and Bockman, R. S. "Prostaglandin $E_1$ Inhibits Collagenase Gene Expression in Rabbit Synoviocytes and Human Fibroblasts," *Endocrinology* 131:001–008 (1992) show that $PGE_1$, but not $PGE_2$ or $PGF_{2\alpha}$, reduced collagenase gene expression leading to decreased collagenase activity. Based on an analysis of such data, applicant discovered that selective administration of $PGE_1$ or cyclic adenosine monophosphate and their agonists and inducers provides unique therapeutic options for the treatment of aging, arthritis, and osteoporosis, major medical problems affecting millions of Americans.

1. Structural importance of collagen and collagenase in cartilage.

Collagen is an important structual component of cartilage. Type II and IX Collagen and Hyaluronic Acid comprise half the dry weight of articular cartilage; proteoglycans constitute the bulk of the remainder (Krane, S. M. "Introduction to rheumatic diseases." In *Scientific American Medicine*, pp. 1–10, Rubinstein, E. and Fedeman D. D. (eds.), a Scientific American publication (1990)). The extracellular matrix of cartilage is comprised of a proteoglycan gel trapped within a tight network of collagen fibrils. The compressibility of this cartilage is largely derived from the proteoglycan gel. Depletion of proteoglycans reduces cartilage compressibility rendering the cartilage more susceptible to mechanical failure (wear) and destruction. Loss of the cartilage proteoglycan occurs early in the arthritic joint with disordered collagen metabolism playing a permissive role in this proteoglycan loss and subsequent cartilage destruction. Damage to cartilage collagen weakens matrix architecture and accelerates proteoglycan loss. Loss of cartilage collagen is particularly notable in the arthritic joints in regions contiguous to the synovial pannus, at surfaces exposed to synovial fluid, and at midzone-pericellular regions (Kobayashi, I. and Ziff, M. "Electron microscopic studies of the cartilage-pannus junction in rheumatic arthritis." *Arthritis Rheum.* 18:475–483 (1975)).

The events needed to pathologically disassemble cartilage can be appreciated by examining an osteoarthritic model in the dog (Pond, M. J. and Nuki, G. "Experimentally induced osteoarthritis in the dog." *Ann. Rheum. Dis.* 32:387–388 (1973)). Following the sectioning of the anterior cruciate ligament in the hind limb there is a "loosening" of the cartilage matrix associated with an increase in water content and the more facile extractability of proteoglycans. Concomitantly there is a measured increase in collagenase activity associated with a disruption of the collagen matrix at the midzone, perilacunar region of the femoral condyles (Pelletier, J. P.; Martel-Pelletier, J.; Altman, R. D.; Ghan dur-Mnaymneh, L.; Howell, D. S. and Woessner, Jr., J. F. "Collagenolytic activity and collagen matrix breakdown of the articular cartilage in the Pond-Nuki dog model of osteoar thritis." *Arthritis Rheum.* 26:866–874 (1983)).

Observations from such studies suggest that there is a common sequence in the pathogenesis of arthritis-mediated joint destruction. The initial step is a decrease in the strength of the collagen network which is thought to result from collagenase activation with a consequent loss (release from encasement) of proteoglycan. Once the collagen network has been compromised, the remaining matrix components of cartilage become increasingly more susceptible to proteolysis by the adjacent synoviocytes and chondrocytes with a progressive loss of collagen and proteoglycans. Indeed, it is very likely that disordered collagen metabolism is a central pathogenic mechanism leading to cartilage destruction. Moreover, subchondral bone resorption which is frequently associated with acute and chronic arthritic destruction of joints is probably triggered by enhanced collagenase production. It is also possible that depressed synthesis of Type I collagen could result in a decreased ability of the subchondral bone to repair itself.

2. Collagenase (EC3.4.24.7).

Collagenase or matrix metalloproteinase 1 (MMP-1) produced by synovial cells (fibroblastic cells lining the joint space) plays a major role in arthritis-induced articular cartilage and subchondral bone destruction. MMP-1 is the only enzyme capable of cleaving the helical regions of Type I (bone) and Type II (cartilage) collagen and therefore has an obligate role in the breakdown of bone and cartilage (Harris, Jr., E. D.; Welgus, H. G. and Krane, S. M. "Collagenase." *N Engl J Med* 291:557–563 (1974)). Cytokines such as IL-1 and TNF, as Well as the tumor promoter phorbol ester (TPA), greatly enhance collagenase gene transcription. Studies have shown that a TPA responsive element (TRE), a 9-nucleotide base sequence in the 5' flanking regulatory (promoter) region of the collagenase gene, serves as the core of an inducible enhancer of gene expression (Stephenson, M. L.; Goldring, M. B.; Birkhead, J. R.; Krane, S. M.; Rahmsdorf, H. J. and Angel, P. "Stimulation of procollagenase synthesis parallels in creases in cellular procollagenase mRNA in human articular chondrocytes exposed to recombinant interleukin 1 or phorbol ester." *Biochem. Biophys. Res. Commun.* 144:583-590 (1987)). The DNA-binding protein (AP-1) which binds to the TRE and activates the gene is a dimer made up in part of members from two families of proteins Fos and Jun. These proteins are products of their respective proto oncogenes (early regulatory genes) c-fos and jun (Rauscher, III, F. J.; Cohen, D. R.; Curran, T.; Bos, T. J.; Vogt, P. K.; Bohmann, D.; Tjian, R. and Franza, Jr., B. R. "fos-associated protein p39 is the protein product of the c-jun oncogene." *Science* 240:1011-1016 (1988)). The intracellular signaling responsible for regulating collagenase transcription is poorly understood. Presumably, TPA and the cytokines IL-1 and TNF activate collagenase gene expression via the protein kinase C (PKC) pathway, but the precise role of PKC in IL-1 signaling is not clear. TNF and IL-1 stimulate endogenous $PGE_2$ synthesis in fibroblasts and osteoblasts. In the fibroblast, $PGE_2$ produces a rise in intracellular cAMP, however, blocking the synthesis of $PGE_2$ with indomethacin was not correlated with changes in collagenase activity (Postlethwaite, A. E.; Raghow, R.; Stricklin, G. P.; Poppyton, H.; Seyer, J. M. and Kang, A. H. "Modulation of fibroblast function by interleukin 1 increased steady state accumulation RNAs and stimulation of other functions but not chemotaxis by human recombinant interleukin 1 alpha and beta." *J. Cell Biol* 105:311-317 (1988)). Therefore, the role of endogenous prostaglandins and in particular, $PGE_2$ in TPA, cytokine-stimulated or basal collagenase activation in synoviocytes and fibroblasts is not understood.

The prior art discussed above, suggests that, if anything, prostaglandins should have a positive or neutral effect on the activity of collagenase. Prior to applicant's discovery, nothing in the art suggested that prostaglandins would have a beneficial, negative effect on the activity of collagenase.

3. Cytokines.

The cytokines, Interleukin-1 (IL-I) and tumor necrosis factor (TNF) are synthesized in large amounts by inflammatory cells as well as by cells lining the joint spaces. These cytokines are thought to play an important role in arthritis associated joint destruction. Firstly, elevated levels of these cytokines are found in the synovial fluid of osteoarthritic and rheumatoid arthritic joints. Secondly, exogenously added cytokines accelerate cartilage destruction, IL-1 and TNF enhance the production of neutral metalloproteinases and serine proteases by chondrocytes and synovial fibroblasts. These enzymes are capable of degrading collagen and proteoglycans. Thirdly, these cytokines inhibit the synthesis of new matrix components thereby delaying bone and cartilage repair, Saklatvala et. al, supra. Lastly, IL-1 and TNF stimulate chondrocytes, synovial cells and osteoblast to produce other endogenous mediators or enhancers of inflammation such as Interleukin 6 (IL-6) and prostaglandins. Elevated IL-6 secretion may initiate the dysplastic changes that are frequently seen in the arthritic joint, while endogenous prostaglandins can augment and enhance the inflammatory response.

4. Prostaglandins in connective and support tissue.

Several eicosanoids are known to be synthesized by cartilage and bone cells and to affect their function. $PGE_2$ is reported to be the major prostaglandin product of synoviocytes, chondrocytes and bone cells and its synthesis can be markedly enhanced by specific cytokines such as IL-1 and TNF (Shinmei, M.; Masuda, K.; Kikuchi; et. al "The role of cytokines in chondrocyte mediated cartilage degradation." *J. Rheumatol. (Suppl)* 18:32-34, (1989)). There is little information as to whether $PGE_1$ is endogenously produced by these cells. While $PGE_2$ is frequently considered to be a catabolic agent and a mediator or amplifier of the inflammatory response, it can have anabolic and protective effects in cartilage and bone. For example, exogenously added $PGE_2$ can inhibit IL-1 release. This has led investigators to propose that $PGE_2$ functions as a feedback regulator of IL-1 secretion. A similar feedback role had previously been described with colony stimulating factor and the hemopoietic precursors (Kurland, J.; Bockman, R. S.; Broxmeyer, H. and Moore, M. "Limitation of excessive myelopoiesis by the extrinsic modulation of macrophage derived prostaglandin E." *Science* 199:552-555 (1978)). Another prostaglandin that is endogenously produced by cartilage and bone cells albeit in much lower amounts is prostaglandin $F_{2\alpha}$ ($PGF_{2\alpha}$). Prostaglandin $F_{2\alpha}$ was found to increase osteoblast proliferation (Hakeda, Y.; Hotta, T.; Kurihara, N.; Ikeda, E.; Maeda, N.; Yagyu, Y.; Kumegawa, M. "Prostaglandin $E_1$ and $F_{2\alpha}$ stimulate differentiation and proliferation, respectively, of clonal osteoblastic MC3T3-E1 cells by different second messengers in vitro." *Endocrinology* 121:1966-1974 (1987)). This action of $PGF_{2\alpha}$ was associated with increased phosphoinositol metabolism leading to the rapid release of inositol phosphates, diglycerides and an increase in cytosolic calcium. Such actions of $PGF_{2\alpha}$ would be anticipated to activate protein kinase C pathways within the cell and lead to the transcription of early regulatory genes such as fos and jun. $PGE_1$ in the same model osteoblast system (the MC3T3-E1 mouse osteoblast) had very different effects. $PGE_1$ enhanced cell differentiation to yield a more mature osteoblastic phenotype (Hakeda, et. al, supra). Stimulation of osteoblastic differentiation was associated with an activation of adenyl cyclase, ibid, and presumably protein kinase A-dependent pathways within the cell. In the osteoblastic MC3T3-E1 cell line, activation of these distinct intracellular signaling pathways was associated with very different outcomes in terms of cell ontogeny and ultimately for the connective tissue matrices they produced. Notably, $PGE_1$ produced a more mature cell that was capable of producing more matrix, whereas $PGF_{2\alpha}$ led to cell proliferation.

When human chondrocytes are treated with $PGE_1$, the expression of Type II cartilage collagen is enhanced (Goldring, M. B. and Krane, S. M. "Modulation by recombinant interleukin-1 of synthesis of types I and III collagens and associated procollagen mRNA levels in cultured human cells." *J. Biol. Chem.* 262:16724-16729 (1987)). In contrast, exposure of human chondrocytes to IL-1 resulted in a decrease in the expression of the cartilage specific collagens Type II and Type X collagen genes (Goldring, et. al, supra).

Thus $PGE_1$ was anabolic and led to new matrix collagen synthesis. In an experiment using artificial gene construct, IL-1 had the opposite effect; it depressed Type II collagen synthesis and activated catabolic enzymes, such as collagenase, that lead to matrix collagen degradation (Stephenson, et. al, op cit., Lafyatis, R.; Seong-Jin, Kim.; Angel, P.; Roberts, A. B.; Sporn, M. B.; Karin, M. and Wilder, R. L. "Interleukin-1 stimulates and trans-retinoic acid inhibits collagenase gene expression through its 5' activator protein-1-binding site". *Molecular Endocrinology* 4:973-980 (1990)). Blocking endogenous prostaglandin synthesis did not alter the ability of IL-1 to activate collagen production. Thus the results of earlier research suggested that endogenous prostaglandins are not protective against IL-1's harmful effect of stimulating collagenase production (Postlethwaite, et. al, supra).

Nevetheless, in accordance with the present invention, the pharmaceutical administration of prostaglandins results in a decrease in collagenase production. The studies summarized in the examples below demonstrate that $PGE_1$ is clearly anti-catabolic in that it inhibits collagenase gene expression in the synoviocyte and fibroblast.

5. Cyclic AMP (cAMP) in connective and support tissue.

As previously noted IL-1 stimulates collagenase gene expression by synovial cells an action that is similar to the effect of phorbol tumor promoters. The molecular action of the active phorbol esters is via their ability to mimic the effect of diglycerides, an intracellular second messenger released during phospholipid metabolism. Both diglycerides and phorbol esters activate protein kinase C and subsequently act through specific families of trans-acting factors (DNA/binding proteins). These proteins target to nuclear DNA where they recognize and bind to response elements (DNA sequences) in their responsive genes. The collagenase gene has such a phorbol ester response element (TRE) and is capable of being activated by phorbol esters and diglycerides, as well as IL-1 and TNF, (Brenner, D. A.; O'Hara, M.; Angel, P.; Chojkier, M. and Karin, M. "Prolonged activation of jun and collagenase genes by tumor necrosis factor-alpha". *Nature* 337:661–663 (1989)). In the case of the collagenase gene, the trans-acting protein, AP-1 that binds to the 5'-flanking region of the gene (that is, at the TRE) is a heterodimer coded for by two early regulatory genes c-fos and c-jun.

Activation of adenyl cyclase associated with increases in the intracellular cAMP levels and protein kinase A activation can have effects on cartilage and bone cells that are opposite to those described for the phorbol ester/protein kinase C pathway. Many studies have demonstrated that a unique cAMP response elements (CRE) exists within the 5'-flanking region of specific genes and that a specific DNA binding protein (CREB) can activate these genes, (Imagawa, M.; Chiu, R. and Karin, M. "Transcription factor AP-2 mediates induction by two different signal-transduction pathways: Protein kinase C and cAMP." *Cell* 51:251–260 (1987)). The studies disclosed in the examples below suggest that a cAMP-induced transacting factor acts on restricted sequences in the 5' flanking region of the human collagenase gene causing an inhibitory or repressive effect on collagenase gene expression.

While recent studies on inflammation by other researchers have suggested that prostaglandin $E_1$ and cyclic adenosine monophosphate may reduce inflammatory response (Bednar, M. S.; et. al, "Cyclic AMP-regulating agents inhibit endotoxin-mediated cartilage degradation" *Biochem J* 244:63–68 (1987)). The effect of prostaglandin $E_1$ or cyclic adenosine monophosphate on collagenase activity was not examined. Other more recent reports have suggested that prostaglandin $E_1$ and its analogs could suppress the inflammatory response in rats to monosodium urate crystals (Tate, G.; et. al, "Suppression of Acute inflammation by 15 methyl Prostaglandin $E_1$" *Lab Invest* 59:192–196, 1988). Neither of these studies provide insight into the method or mechanism by which prostaglandin $E_1$ compounds or cyclic adenosine monophosphate inducers can protect and preserve connective and support tissue from aging, osteoporosis or arthritis.

A synthetic analog of prostaglandin $E_1$, methyl $11\alpha,16$-dihydroxy-16-methyl-9-oxyprost-13E-en-1-oate, known as misoprostol is a commercially available agent that is approved for use in the United States for the prevention of NSAID-induced gastric ulcers. Misoprostol's ability to protect against gastric ulcers through its antisecretory action is unrelated to the new uses and proposed mechanism of action of prostaglandin $E_1$ and its analogs or cyclic adenosine monophosphate, its analogs and inducers as set forth herein.

B. Examples, Procedures and Analysis

The scientific basis for the present invention is illustrated by the following specific examples, procedures and analysis which are not intended to limit the scope of the invention.

1. Cell models and cell culture.

Since primary synovial cell preparations are heterogeneous with respect to cell type, a newly described rabbit synoviocyte cell line, HIG-82 was used in these examples. This cell line was derived from a spontaneously transformed synoviocyte from knee joint tissues. Morphologically, HIG-82 cells resemble primary fibroblasts and functionally they produce MMP-1 upon stimulation with TPA (Georgescu, H. I.; Mendelow, D. and Evans, C. H. "HIG-82: an established cell line from rabbit periarticular soft tissue which retains the 'activable' phenotype". *In Vitro Cell & Dev Biol* 24:1015–1022 (1988)).

The HIG-82 rabbit synoviocyte cell line kindly provided by Dr. C. H. Evans of the University of Pittsburg. This cell line arose by spontaneous transformation from a primary cell culture at the tenth passage. Like primary synoviocytes, HIG-82 produces little $PGE_2$, IL-1 or matrix metalloproteinases in the basal (unstimulated) state but produces great amounts of these products when stimulated by TPA or cytokines. These cells are grown in Ham's F-12 medium supplemented with 2.5 millimolar (mM) glutamine, 1.1 mM calcium, 28 mM Hepes, 10% fetal bovine serum (FBS) and antibiotics.

Non-transformed human skin fibroblasts were provided by Dr. L. Staiano-Coico of Cornell University Medical College and their isolation has been described (Madden, M. R.; Finkelstein, J. L.; Staiano-Coico, L.; Goodwin, C. W.; Shires, G. T.; Nolan, E. E. and Hefton, J. M. "Grafting of cultured allogenic epidermis on second- and third-degree burn wounds on 26 patients." *J Trauma* 26:955–962 (1986)). These cells produce Type $\alpha_1$(I) collagen, fibronectin and collagenase, the production of the latter is greatly augmented by treatment with TPA. These cells are grown in MEM supplemented with 10% FBS and antibiotics.

2. Effects of prostaglandins on collagenase mRNA levels in HIG-82 cells.

Figure 1A:
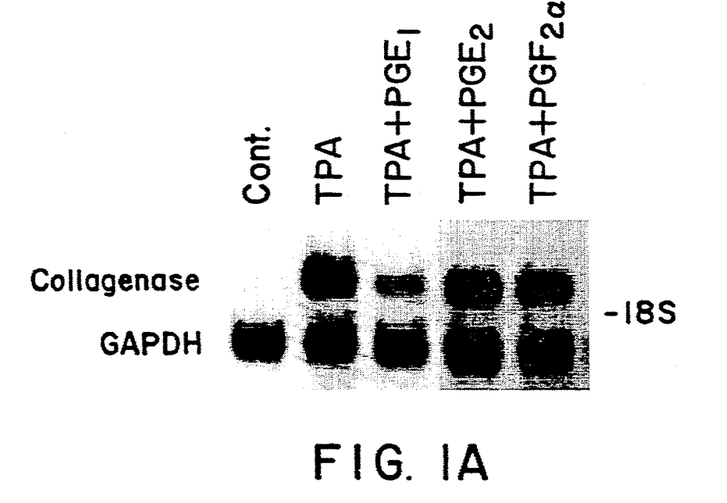
FIG. 1A is a representative photograph of a Northern Blot showing the effects of IBMX, forskolin (FORS) and $PGE_1$ on TPA-stimulated collagenase mRNA in HIG-82 cells.
Figure 1B:
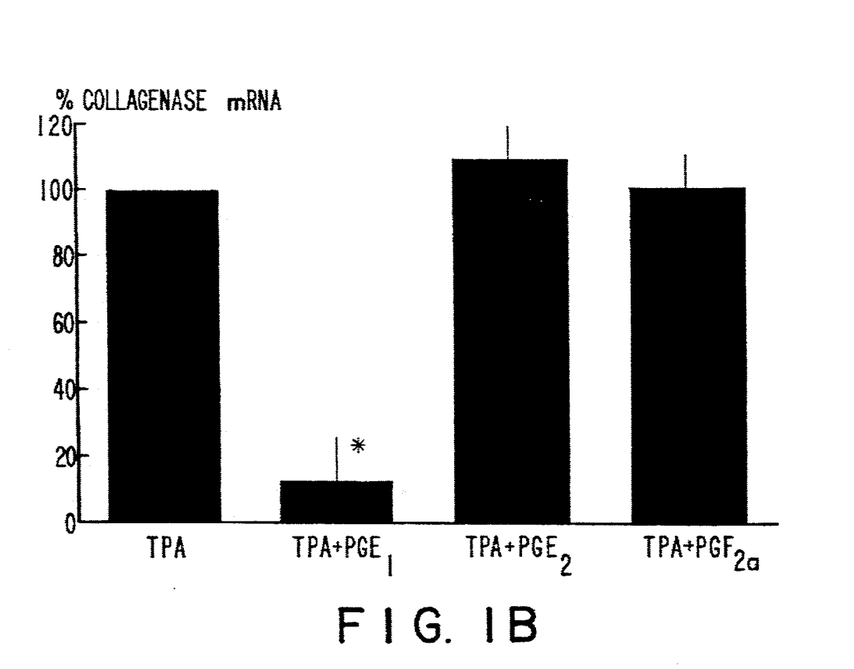
FIG. 1B shows the percentage of TPA-stimulated collagenase mRNA level reduction by IBMX, forskolin (FORS) and $PGE_1$.

HIG-82 synoviocytes were treated for 24 hours with TPA (1 micromolar or 1 $\mu$M) in the presence or absence of 0.001–1 $\mu$M of $PGE_1$. Total RNA was extracted from cell cultures that were approximately 70% confluent. Ten micrograms of total DNA were heat-denatured then size-separated on a MOPS/0.44 M formaldehyde-agarose gel. Ethidium bromide was present in the loading buffer to permit comparisons of the 28S and 18S bands of ribosomal RNA between samples. After electrophoresis, the RNA was transferred to UV- Duralon nylon membranes (Stratagene, LaJolla, Calif.). Adequate transfer was assessed visually by UV-transillumination of ribosomal RNA (rRNA) on the nylon membrane. The RNA was cross-linked to the membrane by a UV-Stratalinker (Stratagene). The blots were treated for 4 hours (h) at 42° Celcius (C.) with prehybridization buffer (50% formamide/ 5xSSPE/ 5x Denhardt's/ 0.1% SDS and 100 μg/ml salmon sperm DNA) and then hybridized for 16-24 h with $^{32}$P-labeled rabbit collagenase cDNA that was kindly provided by Dr. C. Brinkerhoff of Dartmouth Medical College, Hanover, N.H. and with the housekeeping probe, rat glyceraldehyde-3-phosphate dehydrogenase (GAPDH) kindly provided by Dr. L. Pan of Stanford Universty, California. All probes were radiolabeled with $^{32}$P-dCTP by the random priming method. After hybridization and washing to remove unbound probe, Northern Blots were exposed to Kodak XAR-5 film at −70° C. for 1-3 days with intensifying screens. Autoradiographs were scanned by computerized densitometry (Molecular Dynamics, Sunnyvale, Calif.). The Northern Blot shown in FIG. 1A is representative of at least three separate experiments which are summarized in FIG. 1B. As shown, $PGE_1$ drastically reduced collagenase mRNA levels by 75-80%. The effect was dose dependent with a maximal effect seen at 1 μM and a no-effect level around 0.01 μM. No change in GAPDH mRNA levels was seen as indicating that the $PGE_1$-effect was specific for collagenase mRNA. $PGE_2$ and $PGF_{2\alpha}$ had no effect on collagenase or GAPDH mRNA levels when tested at doses as high as 10 μM.

3. Effect of $PGE_1$ on collagenase activity released into the media.

In accordance with the present invention, inhibiting gene expression inhibits collagenase enzyme activities, support for this is found in the following experiment. Previous studies have confirmed a strong correlation between collagenase mRNA levels and enzymatic activity in the HIG-82 cells. Collagenase activity in the media conditioned by HIG-82 cells was measured by growing cells to near confluence, then switching the cells to serum-free Neuman/Tytell media to avoid interference by serum factors. Cells were treated with various effectors and the conditioned media collected after 48 h. Conditioned media (CM) was incubated at 37° C. for 1 h in the presence of 1 mM aminophenylmercuric acetate (APMA) to activate latent collagenase. 10 microliters (μl) of CM was mixed with 10 μl of tritiated rat tail collagen (NEN, Boston Mass., S.A.=0.53 mCi/mg) and 80 μl of reaction buffer 20 mM Tris/HCl pH 7.6 and 5 mM $CaCl_2$ and incubated at 21° C. for 24 h. Undigested collagen was pelleted and 10 μl of the supernatant was counted in a liquid scintillation counter after liquid scintillant was added. Appropriate control samples and blanks of CM from cell-free and non-stimulated cells were tested. The results from three separate experiments, each run in duplicate, showed that CM from untreated cells caused 2.9-2.5% of the radiolabeled collagen to be solubilized (to be enzymatically degraded), the CM from cells treated with TPA (1 μM) caused 16.1-8.9% of the collagen to be degraded, the addition of 1 μM $PGE_1$ to the cell culture, significantly abrogated the TPA effect, resulting in 5.1-6.0% degradation, this reduction was highly significant, p<0.005. Thus there was an excellent correlation between the decrease in collagenase mRNA levels and collagenase activity after treatments with $PGE_1$.

4. Effect of prostaglandins on intracellular cyclic adenosine monophosphate (cAMP) levels.

Figure 2A:
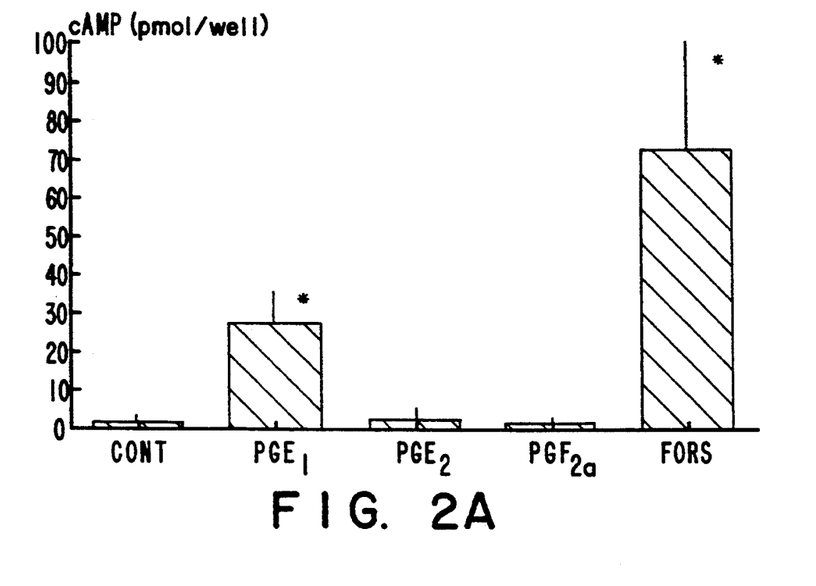
FIG. 2A shows relative effect on the synoviocyte cAMP levels of exposure of HIG-82 cells to $PGE_1$.
Figure 2B:
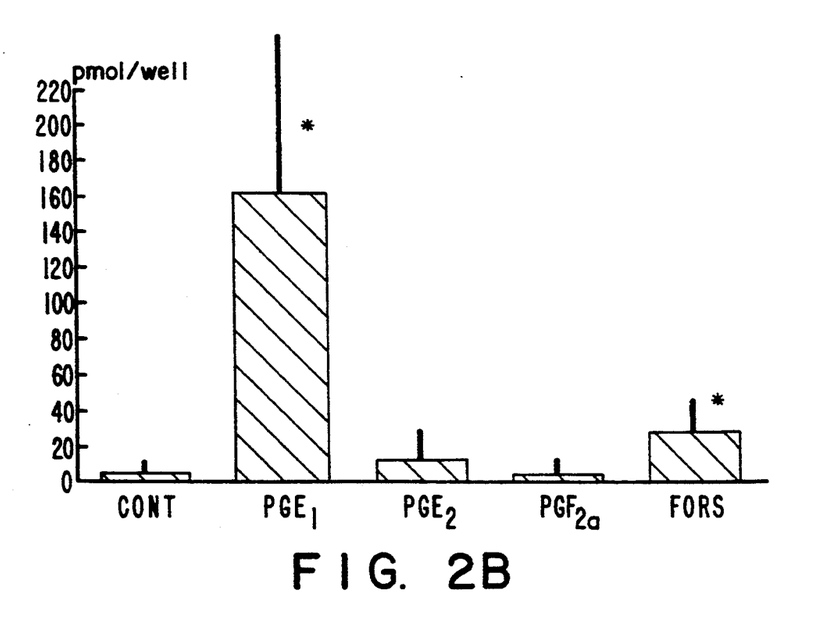
FIG. 2B shows relative effect on the fibroblast cAMP levels of exposure of human skin fibroblasts to $PGE_1$.

HIG-82 cells or human skin fibroblasts were grown as previously described and exposed for ten minutes to various effectors including $PGE_1$ (1 μM), $PGE_2$ (1 μM), $PGF_{2\alpha}$ (1 μm) and forskolin (FORS, 10 μM). cAMP was extracted by ethanol lysis in the presence of 0.5 mM IBMX to prevent degradation of the cAMP in subsequent steps. The soluble intracellular material was recovered after evaporation of the ethanol extract in a Speedvac concentrator (Savant) apparatus. cAMP was determined by radioimmunoassay. The results in FIG. 2A and FIG. 2B are expressed as picomoles/well (pmol/well) as the mean plus or minus the standard deviation (SD) for duplicate samples from three separate experiments. In the HIG-82 cells, FIG. 2A, $PGE_1$ caused approximately a 20 fold and highly significant increase in cAMP levels, whereas $PGE_2$ caused only a modest and non-significant increase. Similar results were obtained with the human skin fibroblasts FIG. 2B. These results support previous studies with $PGE_1$ (Hakeda; et. al, supra), including studies with human synoviocytes (Newcombe, D. S.; Ciosek, C. P.; Ishikawa, Y and Fahey, J. V. "Human synoviocytes: activation and desensitization by prostaglandins and 1-epinephrine." *Proc Natl Acad Sci USA* 72:3124-3128 (1975). However, $PGF_{2\alpha}$ caused no increase in cAMP levels. Forskolin (FORS), a diterpene known to directly activate adenyl cyclase, served as a positive control.

5. Effect of cAMP-inducers on collagenase mRNA levels.

Figure 3:
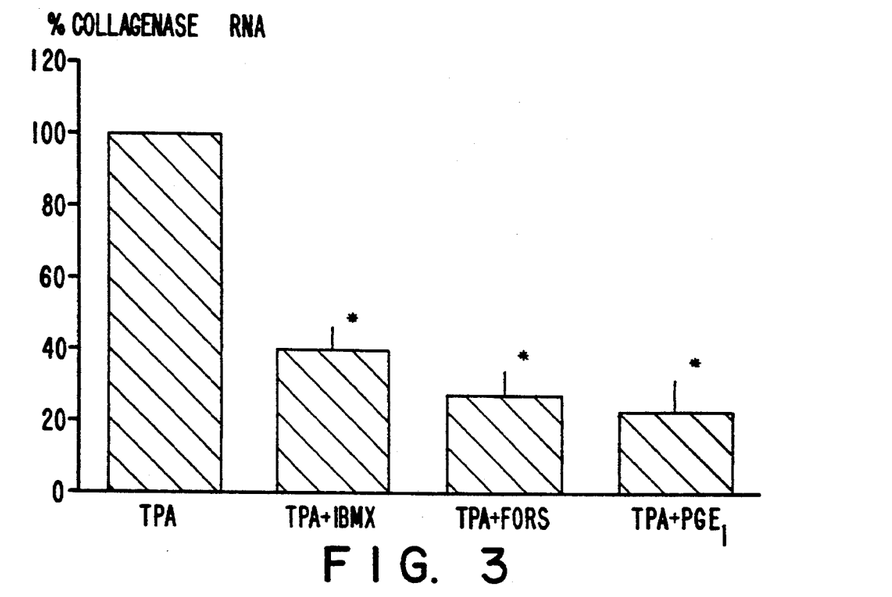
FIG. 3 shows the relative effect of cAMP-inducers on collagenase mRNA levels by quantifying autoradiographs from several experiments and normalizing the results for GAPDH mRNA levels.

To determine whether increases in the levels of cAMP may be mediating the $PGE_1$ effect on collagenase gene expression, the effect of IBMX and FORS on collagenase mRNA levels was measured. Northern Blot analyses were performed on HIG-82 cells treated for 24 h with 100 μM IBMX, which inhibits cyclic nucleotide phosphodiesterase, or 10 μM FORS, which induces adenyl cyclase and thereby increases cAMP levels, and the effects were compared to cells treated with $PGE_1$. All three compounds were able to prevent most of the induction of collagenase mRNA levels by TPA. Autoradiographs from three separate experiments were quantified by computerized densitometry and the results normalized for GAPDH mRNA levels FIG. 3.

6. Effects of $PGE_1$ and cAMP-inducers on human fibroblasts.

To establish whether the effects seen in the HIG-82 cells could be confirmed in another cell type, the human skin fibroblasts, the following procedure was carried out. Cells were used for experiments between passage 2 and 7. Cells were treated for 24 hour with 1 μM $PGE_1$, 10 μM forskolin or 100 μM IBMX. RNA was isolated, blotted and probed as described for the experiments shown in FIG. 1A and FIG. 1B, using human collagenase and rat GAPDH cDNA probes. The results of three separate experiments showed that human fibroblasts produced readily detectable amounts of collagenase mRNA in the basal state; $PGE_1$, forskolin and IBMX reduced collagenase mRNA levels without affecting GAPDH mRNA levels. Therefore, the effect of $PGE_1$ and cAMP-inducers was seen in a human fibroblast cell. The synoviocyte and fibroblast are two of the predominant cell types found in tendons, fascia, ligaments, skin and the lining tissue of joints and these cells are thought to be the major source of the tissue-destructive collagenase. Thus, the beneficial, anti-collagenase formation effects of PGE$_1$ and cAMP inducers were seen with both cell types.

7. Studies with the Collagenase Promoter.

Figure 4A:
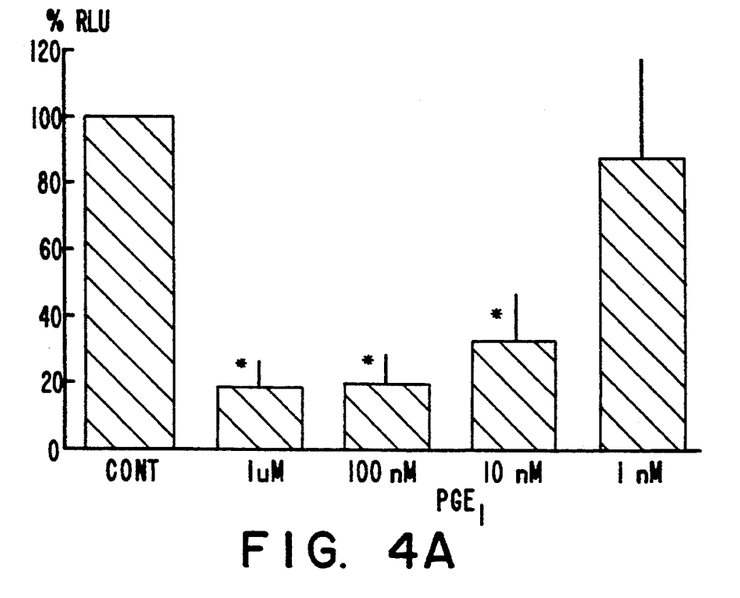
FIG. 4A shows the effect of decreasing concentration of $PGE_1$ on the basal activity of the collagenase promoter.
Figure 4B:
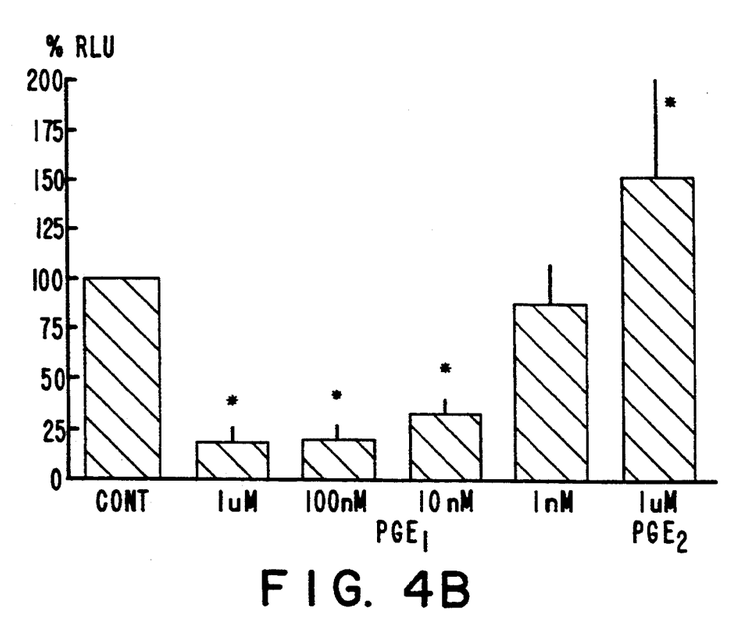
FIG. 4B shows the effect of decreasing concentration of $PGE_1$ on the TPA-stimulated activity of the promoter.

To gain deeper insight into the possible molecular mechanism of the PGE$_1$ and cAMP action on collagenase gene expression, transient transfection experiments using the human collagenase promoter were initiated. HIG-82 cells were transfected with a plasmid pColase-Luc containing a 1.2 kb fragment (−1200 to +63) of the 5'-flanking region of the human collagenase gene, linked to the reporter gene encoding luciferase. This construct was kindly provided by Dr. P. Deutsch of Cornell University Medical College. The pColase-Luc construct was introduced into the cells using the calcium phosphate precipitation method. Calcium phosphate-DNA precipitates were prepared using 3 micrograms (μg) of plasmid DNA. After 4 hours, cells were treated with hypertonic (10%) glycerol solution for 1 minute, washed twice with PBS, and refed with media. Twenty four hours post-transfection, the cells were treated for another 24 hours with the indicated effectors. At the end of the treatment period, cells were harvested and luciferase activity was quantified using a Mono light 2010 luminometer (Analytical Luminescence Laboratories, San Diego, Calif.). Luminescence (light emission) was normalized to total protein. All transfection experiments were repeated three times, and each experimental condition was tested in triplicate. HIG-82 cells transfected with the collagenase-luciferase construct showed an inhibition of the collagenase promoter activity which occurred in a dose dependent fashion in response to PGE$_1$ treatment. This inhibition was seen both under basal FIG. 4A and TPA-stimulated conditions FIG. 4B. Inhibition of basal promoter activity was statistically significant ($p<0.005$–$0.05$ by paired Student's t test) when untreated cells were compared with cells treated with 1 μM, 100 nanomolar (vM) and 10 vM PGE$_1$ FIG. 4A. TPA caused a large induction of the promoter activity FIG. 4B and PGE$_1$ was able to significantly counteract this induction at 1 μM and 100 vM concentrations, PGE$_2$ had no effect at the highest dose tested, 1 μM. These experiments demonstrate that the observed changes caused by PGE$_1$ on collagenase mRNA levels were consequences of transcriptional regulation.

Figure 5:
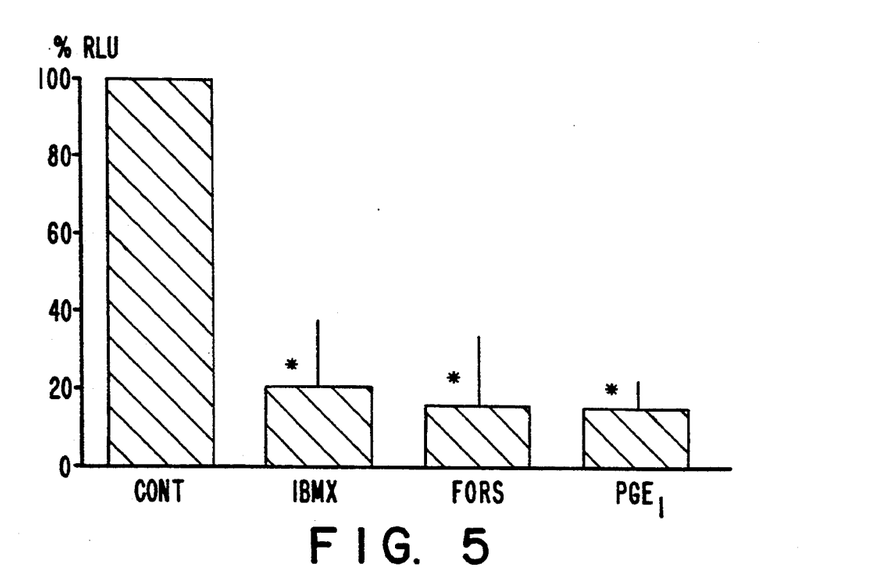
FIG. 5 shows the effects of IBMX, forskolin and $PGE_1$ on human collagenase promoter activity when HIG-82 cells were transfected with the pColase-Luc construct.

In order to verify whether cAMP agonists mimicked the PGE$_1$ effect on the collagenase gene promoter, HIG-82 cells transfected with the pColase-Luc construct were treated with 1 μM PGE$_1$, 10 μM forskolin or 100 μM IBMX. As shown in FIG. 5, all three agents caused a significant reduction of the collagenase promoter activity. Treatment with PGE$_1$, forskolin or IBMX did not significantly change the expression of a Rous Sarcoma Virus promoter (RSV-Luc) construct transfected into HIG-82 cells. The fact that PGE$_1$ and the other cAMP inducers did not influence the expression of the viral promoter-driven RSV-Luc construct demonstrated that their action was specific for the collagenase promoter and that these agents did not influence the stability or the activity of the enzyme luciferase.

8. Preliminary Deletion Analyses.

When the distal 681-basepair fragment (−1200/−520) of the 5'-flanking region from the pColase-Luc construct was deleted the same degree of inhibition by PGE$_1$, forskolin and IBMX was observed as in the original construct to about 20% of the basal activity. This indicates that the response sequences within the promoter region that are responsible for the inhibitory response to PGE$_1$ and cAMP-inducers are probably located in the proximal 519-basepair fragment of the collagenase promoter region. This region has been sequenced (Angel, P.; Bauman, I.; Stein, B.; Delius, H.; Rahmdorf, H. J. and Herrlich, P. "12-O-tetradecanoyl-phorbol-13-acetate induction of the human collagenase gene is mediated by an inducible enhancer element located in the 5'-flanking region." *Mol Cell Biol* 7:2256–2266 (1987)) and does not contain any sequence corresponding to a classical cAMP-responsive element (CRE), that is, a binding site for (CREB), a transacting factor reported to be induced by treatment with cAMP. However, it is important to note that all CRE's identified to date have been associated with a stimulatory effect. Furthermore, the stromelysin gene, another metalloproteinase which is known to be negatively regulated by cAMP in synoviocytes also lacks a consensus CRE (Case, J. P.; Lafyatis, R.; Kumkumian, G. K.; Remmars, E. F. and Wilder, R. L. "IL-1 regulation of transin/stromelysin transcription in rheumatoid synovial fibroblasts appears to involve two antagonistic transduction pathways, an inhibitory prostaglandin -dependent pathway mediated by cAMP, and a stimulatory, protein kinase C-dependent pathway." *J Immmunol* 145:3755–3761 (1990)). Therefore, a novel "inhibitory" cAMP-responsive element appears to exist in the promoter region of these two genes.

9 Recapitulation.

The data contained in these examples show that PGE$_1$ increased cAMP levels in connective and support tissue cells. This elevation in cAMP was associated with a reduction in collagenase mRNA levels and collagenase (MMP1 and probably MMP3) activity. These results suggest that the intracellular mechanism by which PGE$_1$ regulates collagenase gene expression is via cAMP. Indeed, cAMP agonists, such as IBMX and forskolin, caused the same reduction in collagenase gene expression as exerted by PGE$_1$; that is, they reduced collagenase mRNA levels and inhibited the human collagenase promoter expression, mimicking the effect of PGE$_1$. Regulation of collagenase mRNA levels in human skin fibroblasts, by PGE$_1$ and cAMP agonists (forskolin and IBMX) selectively reduced collagenase mRNA levels in these primary human cells and thus reinforced the observations in the HIG-82 cells. Transient transfection experiments using a 1.2 kb fragment of the 5'-flanking region of the human collagenase gene linked to the reporter gene luciferase showed that PGE$_1$ and cAMP-inducers most probably exert their effect on the promoter region of the collagenase gene. The fact that PGE$_1$ and the other cAMP inducers did not influence the expression of the virally driven RSV-Luc construct demonstrated that their action was specific for the collagenase promoter and that these agents did not influence the stability or the activity of the enzyme luciferase. Deletion of the distal 681-basepair fragment (−1200/−520) of the 5'-flanking region from the pColase-Luc construct, reproduced the same degree of inhibition by PGE$_1$, forskolin and IBMX observed in the original construct. This indicates that the region responsible for the inhibitory response to PGE$_1$ and cAMP-inducers is probably located in the proximal 519-basepair fragment of the collagenase promoter region. This region has been sequenced (Angel, et. al. supra) and does not contain a "classical" CRE raising the possibility that within the proximal promoter region, novel inhibitory sequences exist.

These new observations establish the basis for the current invention that $PGE_1$ and its analogs and CAMP and its analogs and inducers have a protective role in protecting and preserving connective and support tissues from the destructive changes caused by aging, metabolic diseases and inflammatory diseases.

The results of the studies presented provide evidence for a novel molecular mechanism and method by which $PGE_1$ preserves and protects connective and support tissues from degenerative effects of inflammation. Applicant believes that the results of the studies may be directly applied to the therapeutic application of pharmaceutically acceptable preparations of prostaglandin $E_1$, analogs of prostaglandin $E_1$ or cyclic adenosine monophosphate agonists or inducers of cyclic adenosine monophosphate to preserve and protect connective and support tissues in humans and animals. The dosages applicable to the utilizaion of the present invention for therapeutic tissue concentrations of the above are believed to range from about one picomolar to about ten millimolar ($10^{-12}M$-$10^{-2}M$), and preferrably from about one hundred nanomolar to about 100 micromolar ($10^{-8}M$-$10^{-4}M$), and yet, more preferrable about one micromolar (1 $\mu M$).

The pharmaceutically acceptable prostaglandin $E_1$ compounds and related compounds that mimic or induce cAMP in cells can be administered topically, transdermally, parenterally, intra-articularly, via the gastrointestinal tract or through the lungs, transbronchially or across the alveoli.

The finding that $PGE_1$, a naturally occurring compound, can similarly inhibit collagenase gene expression along with the clinical availability of therapeutically acceptable long-acting $PGE_1$ analogs open many new therapeutic options. Although preferred embodiments of the present invention have been described above in detail, it is desired to emphasize that this has been for the purpose of illustrating and describing the invention, and should not be considered as necessarily limitative of the invention, it being understood that many modifications can be made by those skilled in the art while still practicing the invention claim herein.

I claim:

1. A method of inhibiting neutral metalloproteinase gene expression in human and animal cells comprising administering a pharmaceutically acceptable prostaglandin $E_1$ compound to said cells.

2. The method of claim 1 wherein said neutral metalloproteinase is collagenase.

3. The method of claim 1 wherein said neutral metalloproteinase is stromelysin.

4. The method of claim 1 wherein said prostaglandin $E_1$ compound comprises a 15-methyl prostaglandin $E_1$ compound.

5. The method of claim 1 wherein said prostaglandin $E_1$ compound comprises a 16-dimethyl prostaglandin $E_1$ compound.

6. The method of claim 1 wherein said pharmaceutically acceptable prostaglandin $E_1$ compound is administered to said cells located in connective or support tissue in an amount so as to achieve a local tissue level of from about 1 picomolar to about 10 millimolar.

7. The method of claim 1 wherein said pharmaceutically acceptable prostaglandin $E_1$ compound is administered to said cells located in connective or support tissue in an amount so as to achieve a local tissue level of from about 100 nanomolar to about 100 micromolar.

8. The method of claim 1 wherein said pharmaceutically acceptable prostaglandin $E_1$ compound is administered to said cells located in connective or support tissue in an amount so as to achieve a local tissue level that is about 1 micromolar.

9. The method of claim 1 wherein said human and animal cells are derived from connective or support tissues.

* * * * *